US006427688B1

(12) United States Patent
Ligotke et al.

(10) Patent No.: US 6,427,688 B1
(45) Date of Patent: Aug. 6, 2002

(54) DRY POWDER INHALER

(75) Inventors: Michael Ligotke; Andrew W. Gieschen; Robert F. Eisele; Thomas R. Jackson, all of San Diego, CA (US); Jeffrey Chen, Seattle, WA (US); Bernard Greenspan, San Diego, CA (US); Clyde Witham, San Diego, CA (US); Gary Ward, San Diego, CA (US)

(73) Assignee: Dura Pharmaceuticals, Icn., San Diego, CA (US)

( * ) Notice: Subject to any disclaimer, the term of this patent is extended or adjusted under 35 U.S.C. 154(b) by 0 days.

(21) Appl. No.: 09/495,494

(22) Filed: Feb. 1, 2000

(51) Int. Cl.[7] .............................................. A61M 15/00

(52) U.S. Cl. ............................ 128/203.15; 128/203.12; 128/203.23

(58) Field of Search ....................... 128/203.15, 203.12, 128/203.21, 203.22, 203.23; 604/58

(56) References Cited

U.S. PATENT DOCUMENTS

| | | | | |
|---|---|---|---|---|
| 2,470,297 A | | 5/1949 | Fields | |
| 2,534,636 A | | 12/1950 | Stirn | |
| 3,362,405 A | * | 1/1968 | Hazel | 128/187 |
| 3,861,210 A | * | 1/1975 | Griverus | 73/194 |
| 4,452,239 A | * | 6/1984 | Malem | 128/200.17 |
| 4,509,515 A | | 4/1985 | Altounyan et al. | |
| 4,790,305 A | * | 12/1988 | Zoltan et al. | 128/200.23 |
| 4,841,964 A | * | 6/1989 | Hurka et al. | 128/203.15 |
| 4,860,740 A | * | 8/1989 | Kirk et al. | 128/203.15 |
| 5,042,472 A | | 8/1991 | Bunin | |
| 5,048,514 A | * | 9/1991 | Ramella | 128/203.21 |
| 5,492,112 A | | 2/1996 | Mecikalski et al. | |
| 5,619,984 A | | 4/1997 | Hodson et al. | |
| 5,642,727 A | | 7/1997 | Datta et al. | |
| 5,714,007 A | | 2/1998 | Pletcher et al. | |
| 5,797,391 A | | 8/1998 | Cook et al. | |
| 6,007,630 A | | 12/1999 | Pletcher et al. | |
| 6,063,194 A | | 5/2000 | Poliniak et al. | |
| 6,073,629 A | * | 6/2000 | Hardy et al. | 128/203.15 |
| 6,074,688 A | | 6/2000 | Pletcher et al. | |
| 6,089,227 A | | 7/2000 | Nilsson | |
| 6,096,368 A | | 8/2000 | Sun | |
| 6,125,998 A | * | 10/2000 | Batista | 206/38 |
| 6,230,707 B1 | * | 5/2001 | Horlin | 128/203.15 |

FOREIGN PATENT DOCUMENTS

| | | |
|---|---|---|
| EP | 0 407 028 A2 | 5/1990 |
| EP | 0 407 028 A3 | 5/1990 |
| EP | 0 504 459 A1 | 9/1992 |
| FR | 2 352 556 | 12/1977 |
| SE | 7509342-7 | 7/1983 |
| WO | WO 90/15635 | 12/1990 |
| WO | WO 95/03846 | 2/1995 |

* cited by examiner

*Primary Examiner*—Aaron J. Lewis
*Assistant Examiner*—Mital Patel
(74) *Attorney, Agent, or Firm*—Lyon & Lyon LLP

(57) ABSTRACT

A dry powder inhaler has a dispersion chamber containing beads. A dose of dry powder is released into the chamber, or into an inlet tangentially joining into the chamber. As the patient inhales on a nosepiece or mouthpiece, air moves circularly through the dispersion chamber to drive the beads. The beads roll, bounce, and collide repeatedly with the drug particles on the chamber surfaces or on the beads. The smaller active drug particles are separated from the larger carrier particles and from each other, and a powder aerosol is created and inhaled by the patient. The beads are preferably lightweight, so that they can be rapidly accelerated and moved, even with nominal inspiration. The flow resistance of the inhaler is also reduced via the beads, allowing greater air flow and powder dispersion, without any increased effort by the patient.

34 Claims, 8 Drawing Sheets

FIG. 1
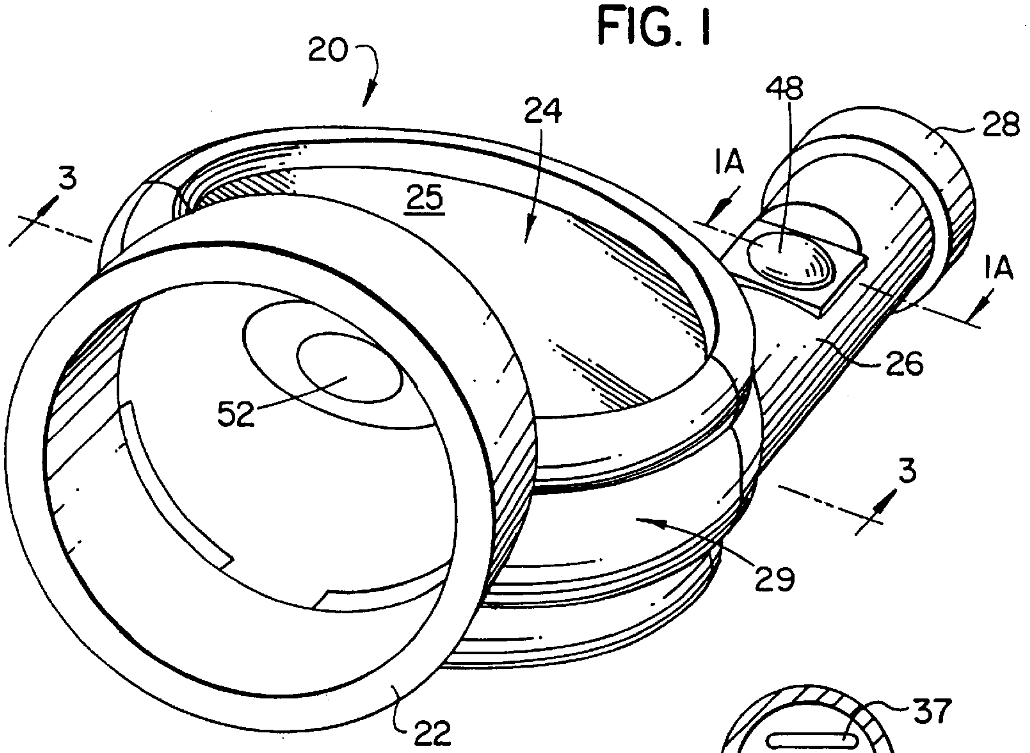
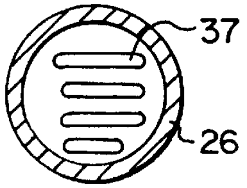
FIG. 1A
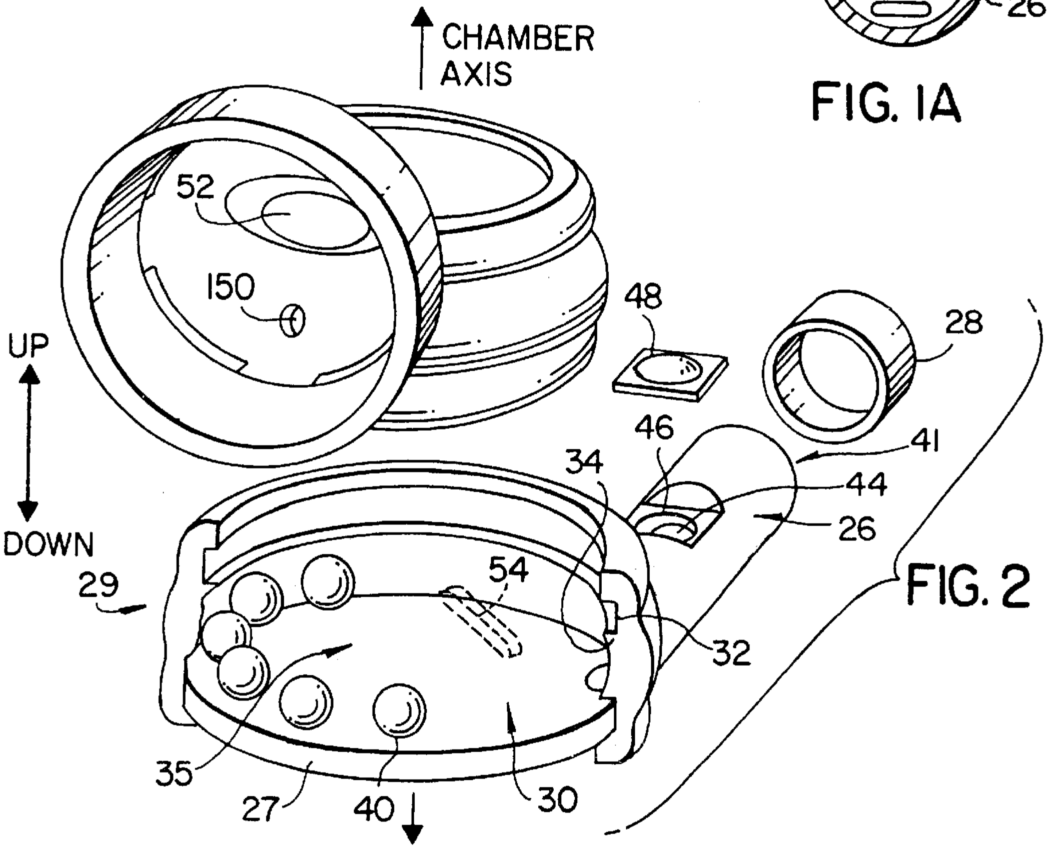
FIG. 2

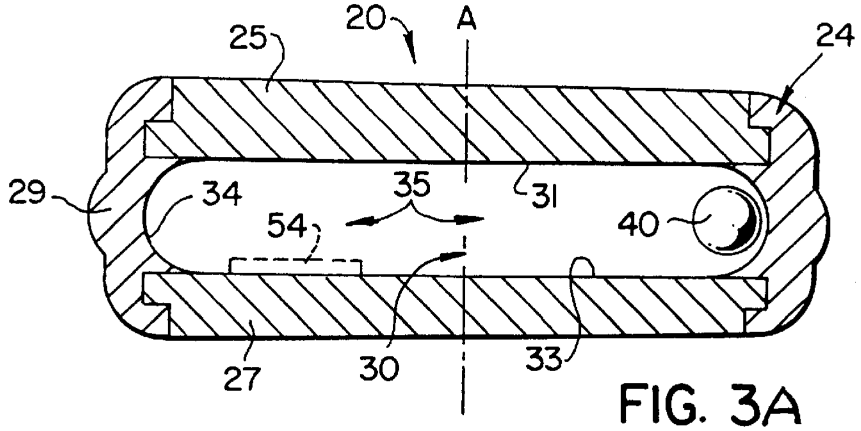
FIG. 3A
FIG. 4
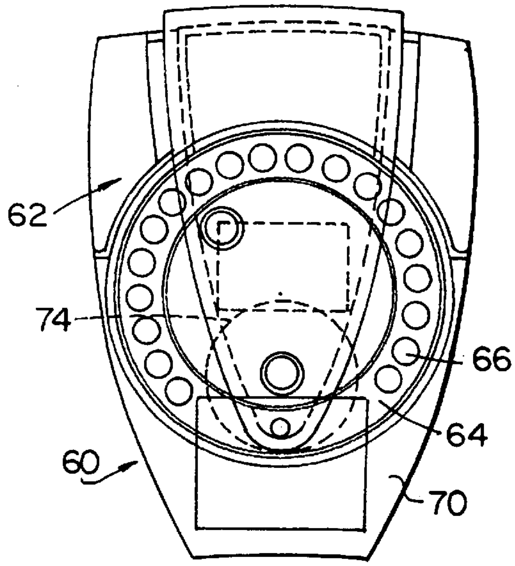
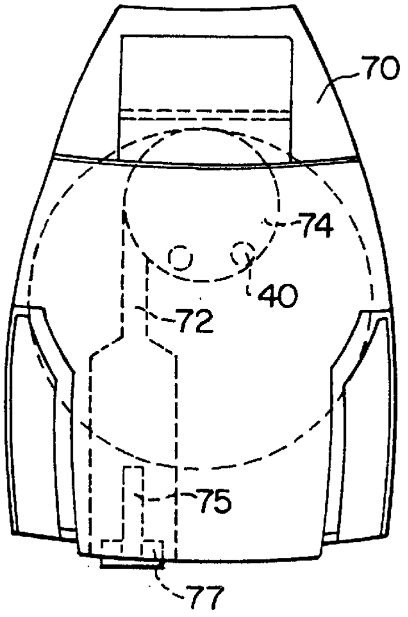
FIG. 7
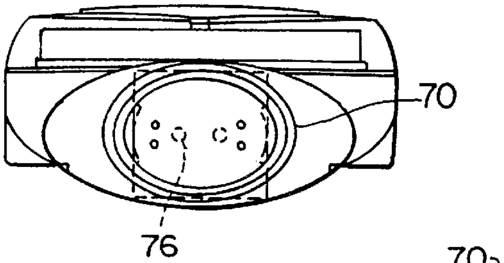
FIG. 5
FIG. 6
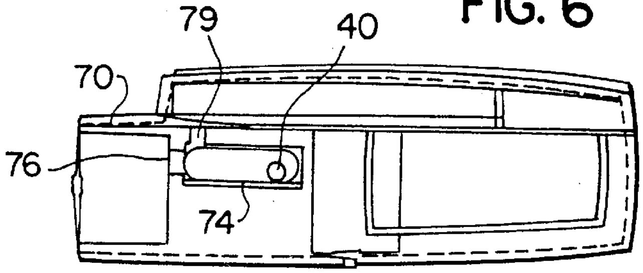

FIG. 8A
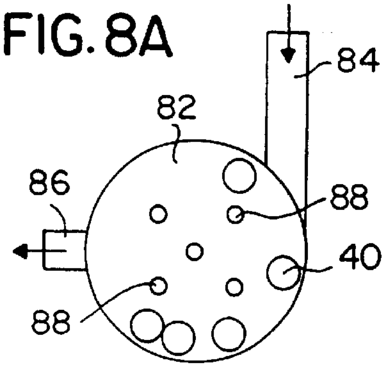
FIG. 8D
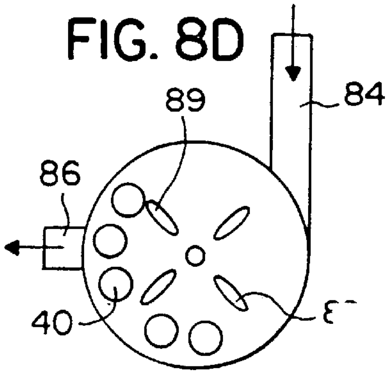
FIG. 8B
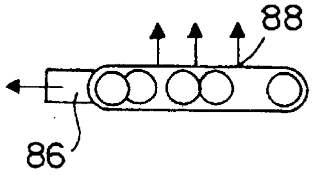
FIG. 8E
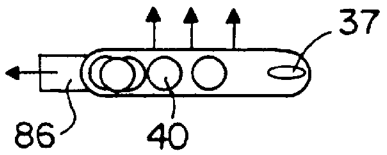
FIG. 8F
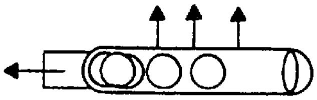
FIG. 8C
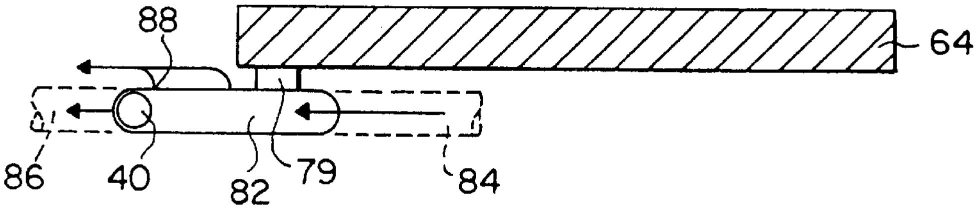
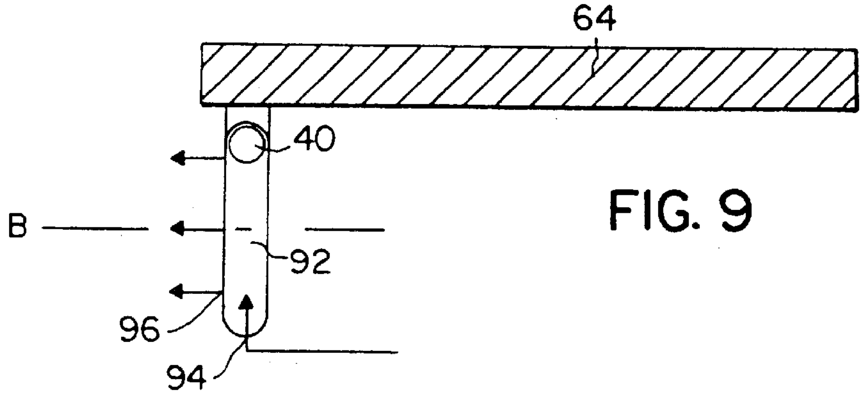
FIG. 9

FIG. 10A
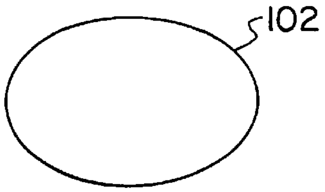
FIG. 12A
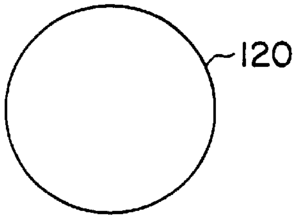
FIG. 10B
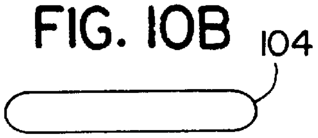
FIG. 12B
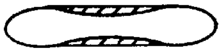
FIG. 11A
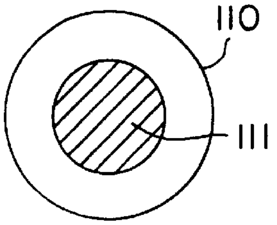
FIG. 13A
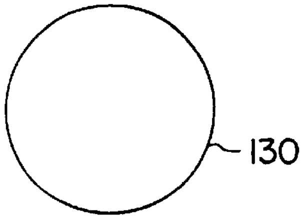
FIG. 11B
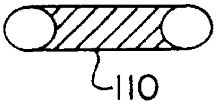
FIG. 13B
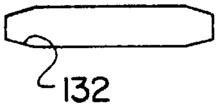
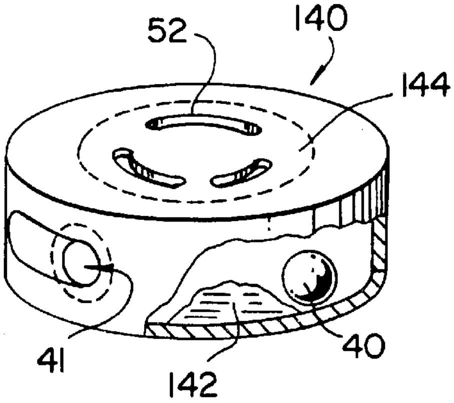
FIG. 14

TABLE: NUMBER OF BEADS VERSUS INHALER RESISTANCE TO AIR FLOW

| | AIR FLOW RESISTANCE (cmH20^0.5/Lpm) | |
|---|---|---|
| NUMBER OF BEADS | ONE-JET INHALER | TWO-JET INHALER |
| 0 | 1.08 | 0.73 |
| 1 | 0.92 | |
| 2 | 0.83 | 0.53 |
| 3 | 0.79 | |
| 4 | 0.76 | |
| 5 | 0.75 | |
| 6 | 0.74 | 0.44 |
| 10 | 0.72 | |
| 11 | 0.72 | |
| 12* | 0.67 TO 1.7 | |

* RESISTANCE MEASUREMENTS FLUCTUATE WHEN 12 OR MORE BEADS ARE USED; THIS IS SHOWN BY THE DASHED LINE IN THE FIGURE.

AEROSOL PERFORMANCE DATA WITH DRY POWDER FORMULATION OF BUDESONIDE AND LACTOSE

| INHALER MODEL | MODEL 1 | MODEL 2 | MODEL 3 |
|---|---|---|---|
| TESTED WITH MOUTHPIECE | NO | YES | YES |
| NUMBER OF AIR JETS IN MODEL | 2 | 1 | 2 |
| TOTAL AIR FLOW, Lpm | 15 | 15 | 28 |
| BEAD CHAMBER AIR FLOW (APPROX.), Lpm | 15 | 9 | 16 |
| AIR-FLOW PRESSURE DROP, cm H2O | 44 | 24 | 51 |
| RESISTANCE, cmH2O^0.5/Lpm | 0.44 | 0.33 | 0.25 |
| RESPIRABLE FRACTION, FIRST SAMPLE, % | 36.2 | 43.1 | 43.6 |
| RESPIRABLE FRACTION, SECOND SAMPLE, % | 34.0 | 43.2 | 43.3 |
| RESPIRABLE FRACTION, THIRD SAMPLE, % | 37.5 | 43.9 | 43.9 |
| RESPIRABLE FRACTION, FOURTH SAMPLE, % | 37.5 | 41.2 | 47.8 |
| RESPIRABLE FRACTION (AVERAGE), % | 36.3 | 42.9 | 44.7 |
| RESPIRABLE FRACTION STANDARD DEVIATION, % | 1.7 | 1.2 | 2.1 |

*FIG. 19*

DRY POWDER INHALER

BACKGROUND OF THE INVENTION

Inhalers are used to deliver drugs into a patient's lungs. Typically, an inhaler contains or provides a mixture of drug particles and air or propellant gas. The mixture is delivered via the patient inhaling from a mouthpiece on the inhaler with the air or propellant gas carrying the drug particles into the patient's lungs.

In dry powder inhalers, the drug particles, in the form of a fine dry powder, are entrained into an airflow, and inhaled by the patient, for treatment for various conditions, for example, bronchial asthma. Drugs delivered via a dry powder inhaler can be used to treat many conditions, including those unrelated to lung conditions, via the systemic absorption of the drug into the bloodstream, via the lung.

For effective dose delivery using a dry powder inhaler, the powder particles must first be dispersed to form a powder/air aerosol. Various techniques for forming powder aerosols have been proposed. Some of these techniques use the airflow from the patient's inspiration alone to disperse the powder. Other techniques involve forming a powder aerosol by spinning a propeller within a chamber; generating a fast moving flow of air over or through the powder; and shaking, vibrating, or impacting a powder laden string, tape, or mesh, using mechanical devices or ultrasonics. In addition, various other techniques for generating powder aerosols have been proposed or used, with varying degrees of success. Challenges remain in achieving a dry powder inhaler which can effectively create a dry powder aerosol for inhalation, while also having advantages in other areas, such as effectiveness in creating an aerosol, reliability, complexity of design, costs, ergonomics, dose consistency, etc.

Accordingly, it is an object of the invention to provide an improved dry powder inhaler.

SUMMARY OF THE INVENTION

To these ends, in a first aspect, a dry powder inhaler has a dispersion chamber. with a central open area surrounded by a bead race. A nosepiece or mouthpiece has at least one outlet opening connecting or entering into the dispersion chamber. One or more inlets also connect into the dispersion chamber. The dispersion chamber contains one or more beads which can move about in the bead race. A powder formulation containing smaller active pharmaceutical particles, and optionally also containing larger inert carrier particles, is placed into or adjacent to the chamber.

When a patient inhales on the mouthpiece, air and powder are drawn into, or flow about within, the dispersion chamber. The beads collide with the interior chamber surfaces, and/or each other, and the powder particles on the chamber surfaces or on the beads. The movement of the beads separate the smaller active drug particles from each other and/or the larger inert carrier particles, if any. In addition to these mechanical forces, other causes of dispersion may include fluid shear between the beads, the powder particles, and the chamber wells. Larger carrier particles, if included in the powder formulation, can further enhance dispersion via enhanced impact energy and abrasion. The active particles are entrained into the airflow through the dispersion chamber, for inhalation by the patient. The larger inert or excipient carrier particles may or may not be entrained and inhaled. The carrier particles are advantageously provided to scour the powder path clean of the fine active particles, so that a more uniform dose may be delivered.

In second and separate aspect of the invention, the beads within the dispersion chamber are induced to move chaotically, so that most or all of the interior surfaces of the dispersion chamber, and the. surfaces of the beads are contacted. As a result, less of the powder may be held up within the dispersion chamber, and a more uniform dose may be delivered. Flow rate performance may also be improved.

In a third and separate aspect of the invention, the flow resistance of a dry powder inhaler is reduced by providing one or more beads into the air flow path of the inhaler. As a result, improved dispersion of powder is achieved, with no additional inspiratory effort by the patient.

BRIEF DESCRIPTION OF THE DRAWINGS

FIG. 1 is a perspective view of a first embodiment of the present inhaler;

FIG. 1A is a section view taken along line 1A—1A of FIG. 1;

FIG. 2 is an exploded section view thereof;

FIG. 3A is a section view taken along line 3—3 of FIG. 1;

FIG. 4 is a top view of a second embodiment;

FIG. 5 is a front view thereof;

FIG. 6 is a side view thereof, in part section;

FIG. 7 is a bottom view thereof;

FIG. 8A is a schematically illustrated top view of a third embodiment;

FIG. 8B is a side view thereof;

FIG. 8C is a side view of the embodiment of FIGS. 8A and 8B, and also schematically showing a dose reservoir or ring;

FIG. 8D is a schematically illustrated top view of the inhaler shown in FIG. 8A, but with elongated or slit outlets;

FIG. 8E is a side view thereof showing a horizontal elongated or slit inlet;

FIG. 8F is an alternative design having a vertical slit inlet;

FIG. 9 is a schematically illustrated side view of another embodiment;

FIG. 10A is a top view of an alternate dispersion chamber, having an oval shape;

FIG. 10B is a side view thereof;

FIG. 11A is top view of an alternate dispersion chamber design, having a toroidal shape;

FIG. 11B is a section view thereof;

FIG. 12A is a top view of an alternative dispersion chamber design having a concave annular shape;

FIG. 12B is a section view thereof;

FIG. 13A is a top view of an alternative dispersion chamber design having a sidewall transition;

FIG. 13B is a side view thereof;

FIG. 14 is a perspective view, in part section, of a separate disposable dose chamber;

FIG. 19 is a table showing aerosol performance of the inhalers shown in FIGS. 1 and 8A.

DETAILED DESCRIPTION OF THE DRAWINGS

Figure 3B:
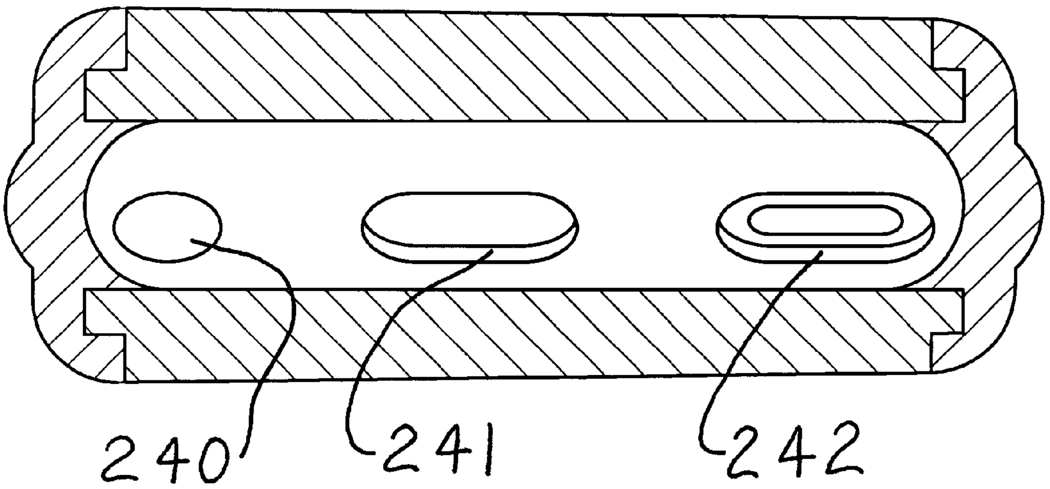
FIG. 3B is a section view taken along line 3—3 of FIG. 1 illustratring alternative bead shapes.

Turning now in detail to the drawings, as shown in FIGS. 1 and 2, an. inhaler 20 has a mouthpiece 22 attached to a housing or body 24. A nosepiece, adapted to engage a patient's nose, may be used in place of the mouthpiece 22, for nasal delivery applications. The term mouthpiece herein means a nose/mouthpiece, i.e., a component adapted. to be placed directly or indirectly on, in, over, or against a patients nose or mouth, or both.

The housing includes a top plate 25, a bottom plate 27, and a circumferential wall 29. An inlet 26 is attached to the housing 24. A flow control device 28 is optionally positioned over the inlet 26. The flow control device 28 may be a flow trigger, or a flow controller or limiter, to moderate air flow into the inlet opening 41.

Referring to FIGS. 1–3, the circumferential wall 29, upper plate 25 and lower plate 27, which make up the housing 24, enclose or define an interior dispersion chamber 30. The dispersion chamber 30 has an open central area 35. A race surface 34 is preferably formed on the inside of the circumferential wall 29. The race surface 34 is a round and smoothly curving surface. The race surface is preferably tangent to the inside (lower) surface 31 of the upper plate 25, as well as tangent to the inside (upper) surface 33 of the lower plate 27, so that the surfaces transition smoothly. The inside surfaces 31 and 33 of the upper and lower plates 25 and 27, are preferably flat and smooth. The upper and lower plates are secured into the housing ring 29 via the plate edges inserting into upper and lower annular slots 32, using adhesives, bonding, ultrasonic welding, or other well known attachment techniques. The housing 24 is preferably made of a plastic material. The housing 24, or the entire inhaler 20, may also be integrally molded or manufactured.

The inlet 26 has an inlet opening or duct 41, preferably joining tangentially into the dispersion chamber 30. The duct 41 may open into the chamber 30 through one or more inlet openings 37, which may be round or elongated slit openings, as shown in FIG. 1A. A dose opening 44 extends through the inlet 26, below a dose platform 46, adapted to receive and hold a dose container 48. Referring still to FIG. 2, one or more outlet openings 52 connect from the chamber 30 to the interior of the mouthpiece 22. The outlets may be configured in the same way as the inlet openings 37, as described above.

The inlet 26 has an inlet opening or duct 41, preferably joining tangentially into the dispersion chamber 30. The duct 41 may open into the chamber 30 through one or more inlet openings 27, which may be round or elongated slit openings, as shown in FIG. 1A. A dose opening 44 extends through the inlet 26, below a dose platform 46, adapted to receive and hold a dose container 48. Referring still to FIG. 2, one or more outlet openings 52 connect from the chamber 30 to the interior of the mouthpiece 22. The outlets may be configured in the same way as the inlet openings 37, as described above.

The beads 40 may be multifaceted large drug particles or irregularly shaped crystalline particles, or amorphous drug particles, so that the drug particles themselves can serve as beads. These bead particles may range in size from e.g., 500 microns to 2–4 mm.

One or more beads 40 are contained within the chamber 30. The beads are preferably spherical, as illustrated in FIG. 3A, but may have other shapes as well, i.e., the beads 40 may be oval or elliptical 240, disk-shaped 241, ring-shaped 242, etc., as illustrated in FIG. 3B. The race surface preferably has a radius of curvature greater than the radius of curvature of the beads 40 (or of the largest bead 40 if the beads are of different size), so that all of the beads can make contact with all surfaces of the race 34. The dispersion chamber 30 preferably holds from 2–10 beads 40. The beads 40 are preferably made of a lightweight material, such as plastic so that they can be rapidly accelerated, and easily moved by the air stream flowing through the chamber 30.

One or more beads 40 are contained within the chamber 30. The beads are preferably spherical, but may have other shapes as well, i.e., the beads 40 may be oval or elliptical, disk-shaped, ring-shaped, etc. The race surface preferably has a radius of curvature greater than the radius of curvature of the beads 40 (or of the largest bead 40 if the beads are of different size), so that all of the beads can make contact with all surfaces of the race 34. The dispersion chamber 30 preferably holds from 2–10 beads 40. The beads 40 are preferably made of a lightweight material, such as plastic so that they can be rapidly accelerated, and easily moved by the air stream flowing through the chamber 30.

The term "characteristic dimension" as used below means the largest dimension (length, width, or height) of the feature or object. Thus, the characteristic dimension of an elliptical bead is the "length" of the bead, i.e., the dimension of the bead taken along its major axis.

The bead 40, or the largest of the beads (i.e., the bead with the largest characteristic dimension) preferably has a characteristic dimension of from 50–90% of the height or thickness of the dispersion chamber, i.e., the dimension between the surfaces 31 and 33. This allows for some vertical bead movement on the race 34, and between the surfaces 31 and 33. The beads can be mixed, with the beads having different sizes, shapes, and materials. In addition, the beads may include one or more "agitator" beads, i.e., a bead with an irregular shape, intended primarily to agitate the other beads, rather than primarily to directly disperse powder.

The chamber 30 preferably has a characteristic dimension (i.e., the diameter for a round chamber; the major axis for an elliptical chamber, etc.) which is from 4 to 20 times greater than the characteristic dimension of the largest bead 40 within the chamber. This allows for sufficient movement of the beads within the chamber, to effectively deagglomerate the drug powder. The beads 40 may be provided with, or manufactured of, a material having a static electrical charge, which may be the same or different to the material of the chamber. The polarity of the charge is selected so that the drug particles are repelled by the beads, to help prevent the particles from sticking to the bead surfaces. The material forming the chamber itself may be similarly charged. The material of the beads and the chamber may be chosen to produce a triboelectric charge upon motion of the beads and air within the chamber. The charge produced may be used to enhance repulsion of the drug particles.

Depending on the specific drug formulation, the bead surfaces may be rough or smooth. Similarly, the beads 40 may be hollow, or solid, or they may be eccentrically shaped, or eccentrically weighted, to achieve desired bead movement and interaction within the chamber 30.

Referring still to FIGS. 1–3, in use, a dose container 48 is placed on the dose platform 46. The dose container 48 is opened releasing a dose of the powdered drug formulation into the inlet 26. The patient inhales on the mouthpiece 22. As this occurs, the optional flow control device 28, if used, opens and air is drawn into the chamber 30 through the inlet opening 41. The dose of powder deposited in the inlet 26 is drawn into the chamber 30 along with the air flowing into the chamber 30. The inflowing air enters tangentially and moves around within the chamber 30. The air movement drives the beads 40 around in the chamber 30. Due to centrifugal force, the beads 40 will move primarily, but not exclusively, along the race 34, rubbing and colliding with the surface of the race 34, as well as with each other, and with the upper and lower surfaces 31 and 33 of the chamber 30. Although the inlet opening 41 extends through the race 34, the diameter of the inlet opening 41 is small enough, in relation to the size of the beads 40, to avoid extensive disruption of the bead trajectories as they pass over the tangential entry point of the inlet opening. Alternatively, the inlet opening 41 can join into the chamber 30 through a plurality of smaller openings, as shown in FIG. 1A.

As the beads 40 move rapidly about within the chamber 30, the contact, collisions, shear effects, etc. disperse the powder formulation. With formulations having excipient or other carrier particles, the moving beads, together with the shear and other effects described above, tend to cause the smaller active drug particles to separate from themselves and/or the larger carrier particles. Referring to FIG. 3A, as virtually all interior surfaces of the chamber 30 can be contacted by the moving beads 40 and the larger carrier or other particles (if any), very little fine powder is held up within the chamber. This means that, most, if not virtually all of the fine powder, initially contained in the dose container 48, is available to be inhaled out of the mouthpiece 22 and inhaled by the patient.

As the beads 40 move rapidly about within the chamber 30, the contact, collisions, shear effects, etc. disperse the powder formulation. With formulations having excipient or other carrier particles, the moving beads, together with the shear and other effects described above, tend to cause the smaller active drug particles to separate from themselves and/or the larger carrier particles. Referring to FIG. 3, as virtually all interior surfaces of the chamber 30 can be contacted by the moving beads 40 and the larger carrier or other particles (if any), very little fine powder is held up within the chamber. This means that, most, if not virtually all of the fine powder, initially contained in the dose container 48, is available to be inhaled out of the mouthpiece 22 and inhaled by the patient.

The beads preferably move with a circulation period determined by the interaction of the air jet with the beads in the chamber. The circulation period is preferably less than about 30 milliseconds. In terms of rpm, the bead velocity is preferably about 500–10,000 rpm in the chamber, and preferably from 2000, 3,000 or 4,000–10,000 rpm. Via the patient's inspiration, the patient inhales (through the nose or mouth) the dispersed powder and air.

As shown in FIGS. 2 and 3, obstructions 54 may be located within the chamber 30, near the race 34, to divert the beads 40 momentarily away from the race 34 (in any direction), to create chaotic bead movement, to better facilitate bead contact with all of the chamber surfaces. Chaotic bead movement means movement of the beads in a less than an entirely uniform manner around the race. The obstructions 54 may be formed as ridges on the surfaces 31 or 33, or as projections on the surfaces 31, 33, or on the race 34. Chaotic bead movement may also be achieved by adjusting other flow parameters to achieve less uniform flow. Specifically, the air inlets 27 can be sized and shaped to cause a transition of bead movement patterns, i.e., with the beads movement changing from more uniform to less uniform, and eventually to chaotic as flow rate increases. This in turn will cause a change in the fine and/or larger particle dispersion efficiencies, with changing flow rates.

Referring momentarily to FIGS. 10A–13B, the chamber 30 may be circular, and disk-shaped (i.e., a cylinder having a diameter greater than its height) as shown in FIG. 2, or it may be elliptical or oval, as shown in FIGS. 10A and 10B; toroidal, as shown in FIGS. 11A and 11B (with a solid or filled in central area 111); or in a biconcave disk shape, that is, round or circular, but curving inwardly towards the center on the top and bottom surfaces (in the shape of a human red blood cell), as shown in FIGS. 12A and 12B; or round with an extended sidewall transition 132, as shown in FIGS. 13A and 13B. Of course, other chamber shapes may also be used, with or without the sidewall transition surfaces connecting the curved race to the flatter surfaces 31 and 33, as shown in FIGS. 13A and 13B.

While FIGS. 1–3 show an inhaler 20 intended for use with discreet individual dose containers 48, FIGS. 4–7 show another inhaler 60 for use with multiple dose containers. Referring to FIG. 4, in the multiple dose container inhaler 60, a dose ring or disk 64 is attached on top of an inhaler housing 62. The dose ring 64 has a plurality of dose containers 66, such as dose wells on a cassette ring, as described, for example, in U.S. Pat. Nos. 5,577,497 and 6,006,747, incorporated herein by reference, or blisters as described, for example, in U.S. Pat. No. 5,622,166, both incorporated herein by reference. Alternatively the inhaler 60 may have bulk powder storage and a dose metering device, as is well known in inhaler technology.

Referring to FIGS. 4–7, the inhaler 60 has an inlet 72 extending into the housing 62 and connecting into a dispersion chamber 74. An outlet 76 at the front end of the dispersion chamber 74 connects into a mouthpiece 70. One or more beads 40 are contained within the dispersion chamber 74, as described above with respect to the inhaler 20 shown in FIGS. 1–3. In use, a dose is released from a dose container 66, passes through a chute or opening 79 and into the chamber 74. The patient inhales on the mouthpiece 70, causing the beads 40, drug dose, and air to move about, producing a powder aerosol for inhalation, as described above.

FIGS. 8A and 8B show an alternative dispersion chamber embodiment which may be used with the inhaler 20 shown in FIGS. 1–3, or with the inhaler 60 shown in FIGS. 4–7. As shown in FIGS. 8A and 8B, an inlet 84 joins tangentially into the chamber 82. The chamber 82 is similar to the chamber 74 shown in FIGS. 4–7, but includes a first or front outlet 86, as well as top outlets 88, connecting to the opening passing through to the mouthpiece 70.

As shown in FIG. 8D, outlets 89 through the top plate 25 may be elongated openings or slits extending radially outwardly. FIG. 8E shows a single horizontal slit opening 37 passing through the circumferential wall 29, connecting the inlet opening 41 into the chamber 30 in contrast to the multiple openings shown in FIG. 1A. A vertical slit opening 43 may also be used, as shown in FIG. 8F.

In the embodiments shown in FIGS. 1–8B, the dispersion chamber is oriented horizontally. The bottom surface 33 is directly underneath the top surface 31, with respect to gravity and the central axis of the chamber, designated A, in FIG. 3A, is vertical. In contrast, as shown in FIG. 9, in an alternative embodiment, the dispersion chamber 92 is oriented vertically, and has a central axis B which is horizontal. Outlets 96 are arrayed along the front surface of the chamber 92, with an inlet 94 at the bottom of the chamber 92.

In the embodiments shown in FIGS. 1–8B, the dispersion chamber is oriented horizontally. The bottom surface 33 is directly underneath the top surface 31, with respect to gravity and the central axis of the chamber, designated A, in FIG. 3, is vertical. In contrast, as shown in FIG. 9, in an alternative embodiment, the dispersion chamber 92 is oriented vertically, and has a central axis B which is horizontal. Outlets 96 are arrayed along the front surface of the chamber 92, with an inlet 94 at the bottom of the chamber 92.

The flow control device 28 may be provided to limit flow, so as to moderate the bead motion within the chamber, as driven by the patient's inspiratory force. The flow control device 28 may be one or more separate components, e.g., it may have a flow control limiter component and a separate flow trigger.

The powder dose may be provided directly in the dispersion chamber 30, 74, 82 or 92, during manufacture of the inhaler, as an alternative to the single dose container 48. Referring to FIG. 14, the dispersion chamber may also be made as a separate component 140 containing beads and a powder dose 142, and insertable into the inhaler, to provide a single dose, for use as a disposable and a replaceable unit. The inlet 41 and outlet 52 are covered with a tape cover 144 or other seal or cover, which is removed before use. Providing the dispersion chamber as a separate removable and/or replaceable component (optionally attached to the mouthpiece) allows the patient to discard or blow out an unintended dose (e.g., a stale dose, a double dose, etc.). It also allows the dispersion chamber to be removed for cleaning the inhaler.

An outlet hole 150 normal to the radial wall of the chamber, as shown in FIG. 2, may be provided, to control the residence time of larger particles within the chamber.

The inhaler may be provided with a feedback device such as a vibrating element, or a whistle or tone generator 75, as shown in FIG. 7. A reed or other vibrating member produces a sound or tactile vibration which turns on or changes in pitch based on the patient's inspiratory flow rate. In this way, the patient can be trained to inhale at the proper flow rate, via the feedback provided by the tactile vibration or sound generated by the patient's inspiration. The feedback device 75 is preferable located at the upstream end of the inhaler. (upstream of the powder path), as shown in FIG. 7. If the feedback device is a sound generator, a button or switch 77 is also preferably provided to allow the patient to switch the sound generator off, so that the inhaler may be used discretely.

For certain applications, the chamber may be manufactured of a transparent material. Upon use, the chamber changes from clear to cloudy or opaque with a predetermined amount of deposited particles, providing a visual indication to the patient that the replaceable chamber has been used.

In a single dose device, for example as shown in FIG. 1, the chamber may have a centrally located outlet, which allows the small active respirable particles to exit out through the mouthpiece, but retains any non-dispersed particles. As the inhaler, or chamber, is used only once, the retention of the non-dispersed particles within the chamber is acceptable. Preferential dispersion and retention of particles may be enhanced through triboelectric charging by selection of appropriate materials.

Figure 15A:
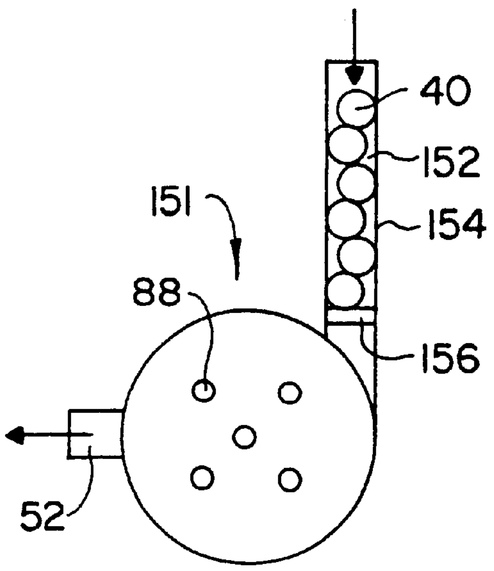
FIG. 15A is a schematically illustrated plan view of an inhaler embodiment having beads stored in a compartment separate from the dispersion chamber, before use.
Figure 15B:
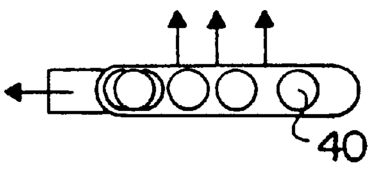
FIG. 15B is a side view thereof.

FIGS. 15A and 15B show an inhaler embodiment 150 having beads 40 stored in a storage compartment 152 within an inlet tube 154. A retainer/flow trigger 156 holds the beads in the compartment. Upon inhalation by the patient, the retainer/flow trigger opens, releasing the beads into the chamber. The beads disperse powder in the chamber, as described above. The sudden release of the beads provides a boost to bead movement and dispersion. The flow trigger 156 or beads 40 can also act as a backflow preventer, to prevent the patient from exhaling into the inhaler. In addition, the presence of the released beads in the chamber and any non-dispersed particles, following delivery of the dose, provides a tactile, visual and sound indication that the inhaler has been used and is spent. The powder may be provided with the beads 40 in the storage compartment, or it may be prefilled into the chamber, or be delivered into the chamber from a cassette, a blister disk or a bulk powder dispenser.

Figure 16A:
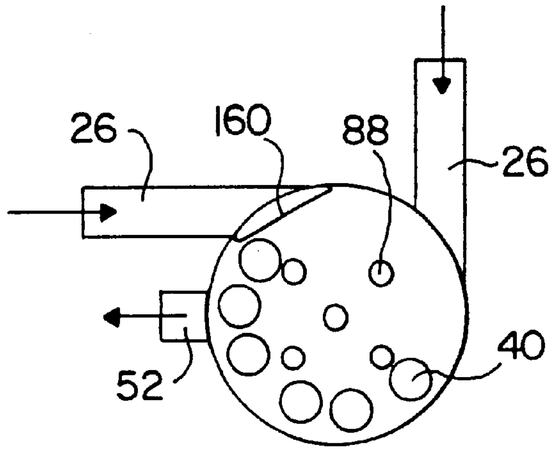
FIG. 16A is a schematically illustrated plan view of an inhaler embodiment similar to the design shown in FIG. 8A, but with two inlets.
Figure 16B:
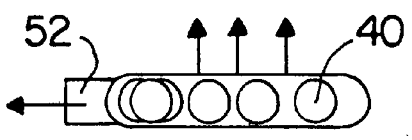
FIG. 16B is a side view thereof.

FIGS. 16A and 16B show a design similar to FIGS. 8A and 8B, but with two radially spaced apart inlets 26. One of the inlets may include a flow trigger 160 which opens only upon reaching a specified threshold of pressure drop or flow rate. The opening of the flow trigger 160 can be used to change the pattern of bead movement.

A surprising result of the inhalers above having beads is that the presence of the moving beads substantially reduces the flow resistance of the inhalers, for both uniform and chaotic bead movement. At 10 liters per minute (lpm) of flow, the reduction in flow resistance is about 15–33%, using from 1–11 beads, compared to flow resistance with no beads, and the reduction is about 23–33% using 2–11 beads. For the embodiment shown in FIG. 16A having 2 inlets, at 10 lpm, using 6 beads, flow resistance was reduced by 40%, when compared to the same inhaler with no beads. This reduction increased to 44% at 15 lpm. These reductions in flow resistance are counterintuitive because the beads reduce the flow cross sections within the inhaler. Thus, one would expect the presence of the beads to increase, rather than decrease, the flow resistance.

This reduction in flow resistance provides the advantage of allowing more air to flow through the inhalers at any given pressure drop (inspiration or suction force of the patient). This increase in flow increases powder dispersion, without any increase in patient effort.

Figures 17, 18:
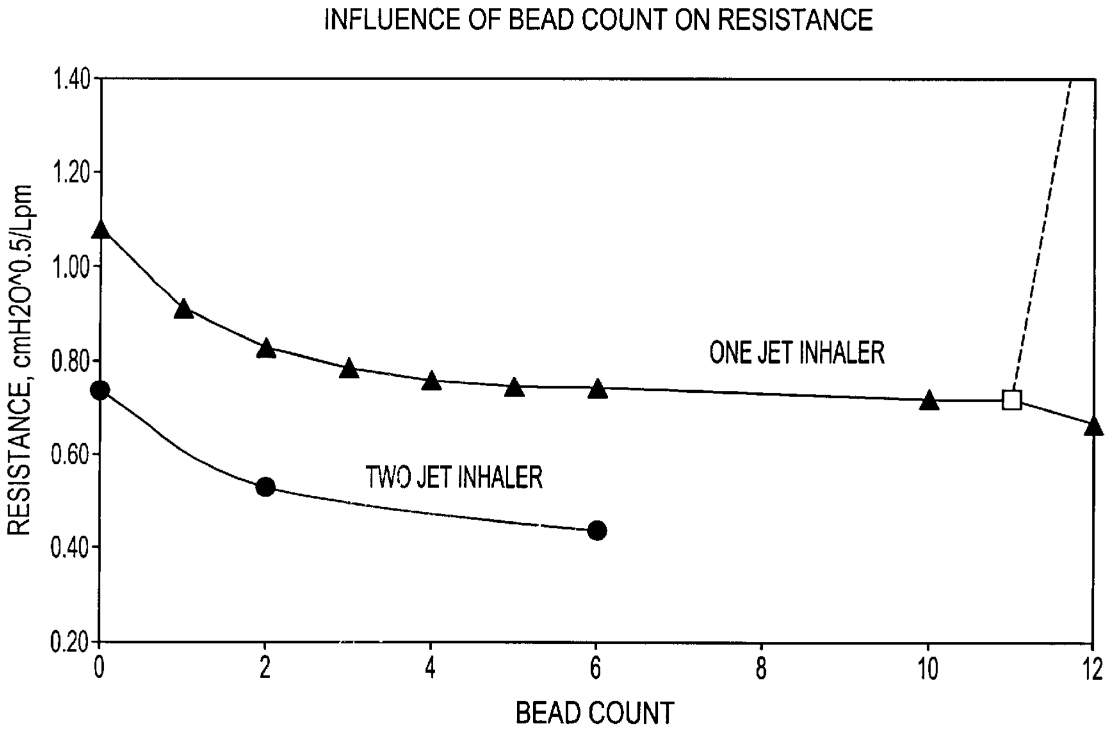
FIG. 17 is a table of air flow resistance data for the inhalers shown in FIGS. 1 and 8A.
FIG. 18 is a graph of the data shown in FIG. 17.

FIG. 17 shows data on the reduction of flow resistance via use of beads, for one and two jet (inlet) inhalers, as shown in FIGS. 1 and 16A. FIG. 18 shows the data in graphical form.

FIG. 19 shows in-vitro aerosol performance data for the inhalers with one and two inlets or jets, as shown in FIG. 1 and 16A. Using dry powder formulations of budesonide and lactose resulted in budesonide respirable fractions between 34–48%, as shown in FIG. 19. Each of the 3 inhalers were tested with a total of 4 separate aerosol samples. The average and standard deviation of respirable fraction for each model was 36.3±1.7% (Model 1), 42.9±1.2% (Model 2), and 44.7±2.1% (Model 3). Thus, the inhaler performance, in terms of respirable fraction, air flow resistance, powder holdup, and reproducibility of dose, is very good, in comparison to existing inhalers.

Thus, a novel inhaler and methods have been shown and described. The inhaler provides various advantages. It can be manufactured at low cost, provide quiet operation to enhance patient discretion, and reduce hold up of powder within the inhaler, as a result of the self-cleaning/scouring action of the beads. The present inhaler also has reduced size and weight, yet has a high efficiency in delivering a dose of dry powder.

Various changes and modifications may of course be made without departing from the spirit and scope of the invention. The invention, therefore, should not be limited, except by the following claims and their equivalents.

What is claimed is:

1. A method for providing a dose of a dry powder pharmaceutical to a patient, comprising the steps of:

providing a dose of dry powder in a dispersion chamber of an inhaler;

moving air through an open central interior of the dispersion chamber; and reducing the flow resistance of air flow through the dispersion chamber, by providing at least one bead in the dispersion chamber, with the bead in the chamber reducing the flow resistance to a level 15–40% less than the flow resistance of the inhaler without any beads in the chamber.

2. The method of claim 1 wherein air is moved through a dispersion chamber having an open central area surrounded by a bead race;

the at least one bead is in the open central area and in the bead race, so that the bead comes into physical contact with at least some of the dose dry powder in the chamber.

3. The method of claim 2 wherein the dry powder pharmaceutical comprises active particles attached to excipient particles, further comprising the steps of:

separating at least some of the active particles from at least some of the excipient particles via contact with the bead and airflow;

mixing air in the chamber with at least some of the separated active particles; and moving at least some of the separated active particles and air out of the chamber.

4. The method of claim 3 further comprising the step of separating the particles via fluid shear effects caused by flowing air and bead motion.

5. The method of claim 3 further comprising the step of dispersing the particles via scouring and impact of particles within the chamber.

6. The method of claim 2 wherein the race has a radius of curvature greater than a radius of curvature of the at least one bead.

7. The method of claim 1 further comprising the step of moving the at least one bead in a chaotic manner around in the chamber.

8. The method of claim 1 further comprising the step of moving the at least one bead around in the chamber by using a patient's inspiration to entrain the at least one bead in an air flow, so that the at least one bead moves chaotically within the chamber.

9. The method of claim 1 further comprising the step of releasing a dose of powder into the chamber before moving the at least one bead therein.

10. The method of claim 1 further comprising the step of releasing a dose of powder into an inlet connecting into the chamber.

11. The method of claim 1 further comprising the step of entraining a plurality of beads in an air flow within the chamber, and causing the beads to intermittently collide with each other and with inner surfaces of the chamber.

12. The method of claim 1 further comprising the step of drawing air through the chamber at first flow rate, thereby causing the at least one bead to move in a uniform manner around the chamber, and drawing the air through the chamber at a second flow rate, greater than the first flow rate, thereby causing the at least one bead to move in a chaotic manner within the chamber.

13. The method of claim 1 wherein the at least one bead has or acquires a static electrical charge, and the dry powder pharmaceutical particles also have or acquire a static electrical charge of the same polarity, so that the at least one bead and the pharmaceutical particles repel each other.

14. The method of claim 1 wherein the chamber is initially free of pharmaceutical powder, further including the step of delivering a dose of powder into the chamber.

15. The method of claim 1 further comprising the step of drawing air through the chamber at first flow rate, thereby causing the at least one bead to move in a uniform manner around the chamber, and transitioning the bead movement from uniform to non-uniform as air flow rate through the chamber increases above the first flow rate, thereby causing the at least one bead to move in a less uniform manner within the chamber.

16. The method of claim 1 further comprising the step of placing the chamber into the inhaler before the drawing air through the chamber step, wherein the chamber is separate, installable into, and removable from the inhaler.

17. The method of claim 1 wherein a plurality of beads are in the chamber, and wherein at least one of the beads includes a discontinuity.

18. The method of claim 17 wherein the bead(s) with the discontinuity is polygonal shaped, and the discontinuity comprises a corner.

19. The method of claim 17 wherein the at least one bead having the discontinuity comprises a sphere with a flat surface.

20. The method of claim 1 further comprising the step of providing feedback to the patient based on air flow rate.

21. The method of claim 1 wherein the dispersion chamber has a flat bottom surface and a flat top surface adjoining the bead race.

22. The method of claim 1 wherein from 2–10 round beads are provided in the dispersion chamber.

23. The method of claim 22 wherein the beads move around the dispersion chamber at 4000–10,000 rpm.

24. The method of claim 1 wherein the chamber has a characteristic dimension which is from 4–20 times greater than a characteristic dimension of the at least one bead.

25. The method of claim 1 wherein an obstruction in the dispersion chamber causes the beads to move chaotically.

26. The method of claim 1 wherein the dispersion chamber has a height H and the bead has a characteristic dimension of 50–90% H.

27. The method of claim 1 wherein the dispersion chamber has a height H and wherein the bead is round and has a diameter of 50–90% H.

28. The method of claim 1 wherein the dispersion chamber has a inner radiused circumferential wall forming a bead race, and wherein the beads move circumferentially around the bead race, upon inhalation by the patient.

29. The method of claim 1 wherein air moves through the dispersion chamber at 10–28 lpm.

30. The method of claim 1 wherein air moves through the dispersion chamber at about 10–15 lpm.

31. A method for providing a dose of a dry powder pharmaceutical to a patient, comprising the steps of:

providing a dose of dry powder in a dispersion chamber of an inhaler;

moving air through an open central interior of the dispersion chamber at a flow rate ranging from 10–28 liters/minute; and reducing the flow resistance of air flow through the dispersion chamber, by providing at least one bead in the dispersion chamber, with the bead in the chamber reducing the flow resistance to a level 15–40% less than the flow resistance of the inhaler without any beads in the chamber.

32. The method of claim 31 wherein the flow rate or air is 10–15 liters/minute.

33. A method for providing a dose of a dry powder pharmaceutical to a patient, comprising the steps of:

providing a dose of dry powder in a dispersion chamber of an inhaler;

moving air at a flow rate through an open central interior of the dispersion chamber;

reducing the flow resistance of air flow through the dispersion chamber, by providing one or more beads in the dispersion chamber, with the beads moving around a race in the chamber and reducing the flow resistance to a level 15–40% less than the flow resistance of the inhaler without any beads in the chamber; and with the flow rate selected so that the beads move in a uniform manner around the race in the dispersion chamber.

34. The method of claim 33 wherein the beads move at 4000–10,000 rpm.

* * * * *